United States Patent
Yoo et al.

(10) Patent No.: US 6,844,436 B2
(45) Date of Patent: Jan. 18, 2005

(54) PREPARING PYRAZOLOPYRIMIDINONE DERIVATIVES FOR THE TREATMENT OF IMPOTENCE

(75) Inventors: Moo-Hi Yoo, Seoul (KR); Won-Bae Kim, Seoul (KR); Min-Sun Chang, Yongin-si (KR); Soon-Hoe Kim, Suwon-si (KR); Dong-Sung Kim, Seoul (KR); Chul-Jun Bae, Seoul (KR); Yong-Duck Kim, Suwon-si (KR); Eun-Ha Kim, Sungnam-si (KR)

(73) Assignee: Dong A. Pharm. Co., Ltd., Seoul (KR)

( * ) Notice: Subject to any disclaimer, the term of this patent is extended or adjusted under 35 U.S.C. 154(b) by 5 days.

(21) Appl. No.: 10/311,397

(22) PCT Filed: May 18, 2001

(86) PCT No.: PCT/KR01/00819

§ 371 (c)(1),
(2), (4) Date: Dec. 11, 2002

(87) PCT Pub. No.: WO01/98304

PCT Pub. Date: Dec. 27, 2001

(65) Prior Publication Data

US 2003/0176696 A1 Sep. 18, 2003

(30) Foreign Application Priority Data

Jun. 23, 2000 (KR) .......................... 2000-34966

(51) Int. Cl.$^7$ .......................... C07D 487/04
(52) U.S. Cl. .......................... 544/262
(58) Field of Search .......................... 544/262

(56) References Cited

FOREIGN PATENT DOCUMENTS

| EP | 0 463 756 | 1/1992 |
|----|-----------|--------|
| WO | 93/06104 | 4/1993 |
| WO | 98/49116 | 11/1998 |
| WO | 00/27848 | 5/2000 |

OTHER PUBLICATIONS

Reusch, William, "Virtual Textbook of Organic Chemistry" Michigan State University, [retrieved on Mar. 2, 2004]. Retrieved from the internet, <http://www.cem.msu.edu/~reusch/VirtualText/amine1.htm>.*
Fu et al, CN 1,246,478, 2000, cited in Chemical Abstracts, AN 133:281797 CASREACT.*
Fu et al, CN 1,246,478, Mar. 8, 2000, English translation PTO 04–2259.*

* cited by examiner

Primary Examiner—Thomas C. McKenzie
(74) Attorney, Agent, or Firm—Bachman & LaPointe, P.C.

(57) ABSTRACT

A method for preparing pyrazolopyrimidinone derivatives and their pharmaceutically acceptable salts having efficacy on the treatment of impotence, one of male sexual dysfunctions. The method comprises the steps of: a) chlorosulfonating a pyrazolamide compound to obtain a chlorosulfonated compound; b) reacting the chlorosulfonated compound of step (a) with a primary amine to obtain a sulfonamide compound and c) performing an intramolecular cyclization of the sulfonamide compound of step (b) to produce the compound of formula below 1, wherein the steps b) and c) are performed in situ in alcohol by adding a base to the reaction mixture without workup after the step b) is completed.

Formula 1

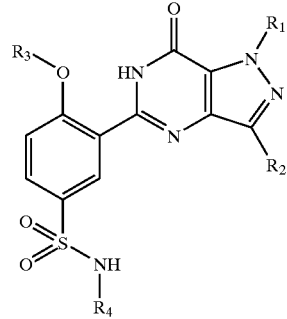

9 Claims, No Drawings

PREPARING PYRAZOLOPYRIMIDINONE DERIVATIVES FOR THE TREATMENT OF IMPOTENCE

TECHNICAL FIELD

The present invention relates to a process for preparing pyrazolopyrimidinone derivatives of formula 1 and pharmaceutically acceptable salts thereof which have an efficacy on impotence, comprising the steps of chlorosulfonation of pyrazolamide compounds of formula 2, followed by amination with a primary amine and intramolecular cyclization.

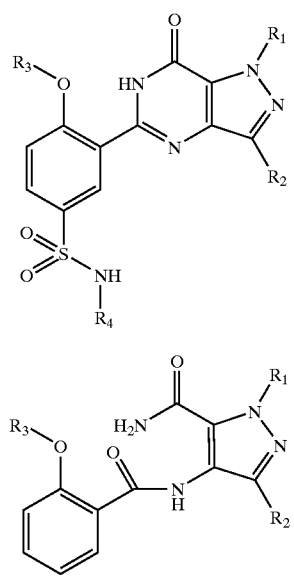

Formula 1

Formula 2

The compounds of formula 1 may exist in tautomeric equilibrium as shown below.

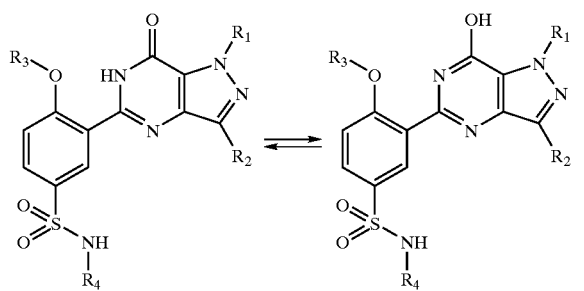

The compounds of formula 1 may also contain asymmetric centers and thus they can exist as enantiomers. The present invention includes both racemic mixture and separate individual enantiomers.

BACKGROUND ART OF THE INVENTION

Male erectile dysfunction is one of the most common sexual dysfunctions in man. Although erectile dysfunction can be primarily psychogenic in origin, it often accompanies chronic illnesses, such as diabetes mellitus, heart disease and a variety of neurological diseases. It is estimated that about 2~7% of the male population are impotent. Its prevalence is strongly related to age. For example, 18~75% of the age group of 55 to 80 years is believed to be impotent.

Various treatment options for erectile dysfunction are available, such as counseling, hormone replacement therapy, self-injection or transurethral application of vasodilator agents, vacuum devices, and vascular surgery. However, these therapeutic options have several limitations such as side effects, high cost and low efficacy.

Recently, Sildenafil has been developed as a therapeutic agent for male erectile dysfuction by oral administration. Sildenafil is the first in a new class of drugs known as inhibiting phosphodiesterase-5 enzyme distributed specifically in corpus cavernosal tissues and induces relaxation of the corpus cavernosal smooth muscle cells, so that blood flow to the penis is enhanced, leading to an erection. Sildenafil has shown a response rate of around 80% in men with erectile dysfunction of organic cause.

Since sildenafil has been developed, various compounds for inhibiting phosphodiesterase-5 have been reported. Among them, pyrazolopyrimidinone compounds of formula 1 (KR Pat. No. 99-49384) were reported having better potency than that of sildenafil, based on the mechanism of inhibiting phosphodiesterase-5 and having better selectivity over phosphodiesterase-6 distributed in retina and phosphodiesterase-3 distributed in heart to reduce the side effects. Further, the pyrazolopyrimidinone compounds of formula 1 were said to be improved the solubility and the metabolism in the liver, which are very important factor affecting the rate of the absorption when administered orally.

The KR patent No. 99-49384 also disclosed a process for preparing the pyrazolopyrimidinone compounds of formula 1, comprising the steps of:

a) reacting chlorosulfonated alkoxy benzoic acid with a primary amine to obtain sulfonamide-substituted benzoic acid;

b) reacting the obtained sulfonamide-substituted benzoic acid with pyrazolamine in the presence of activating reagent of carboxylic group or coupling agent of carboxylic group with amine group to obtain corresponding amide compound; and, c) performing an intramolecular cyclization of the obtained amide compound to obtain the pyrazolopyrimidinone compound of formula 1.

This reaction is represented as follows.

Scheme 1

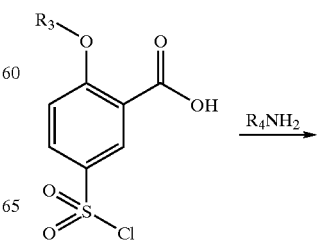

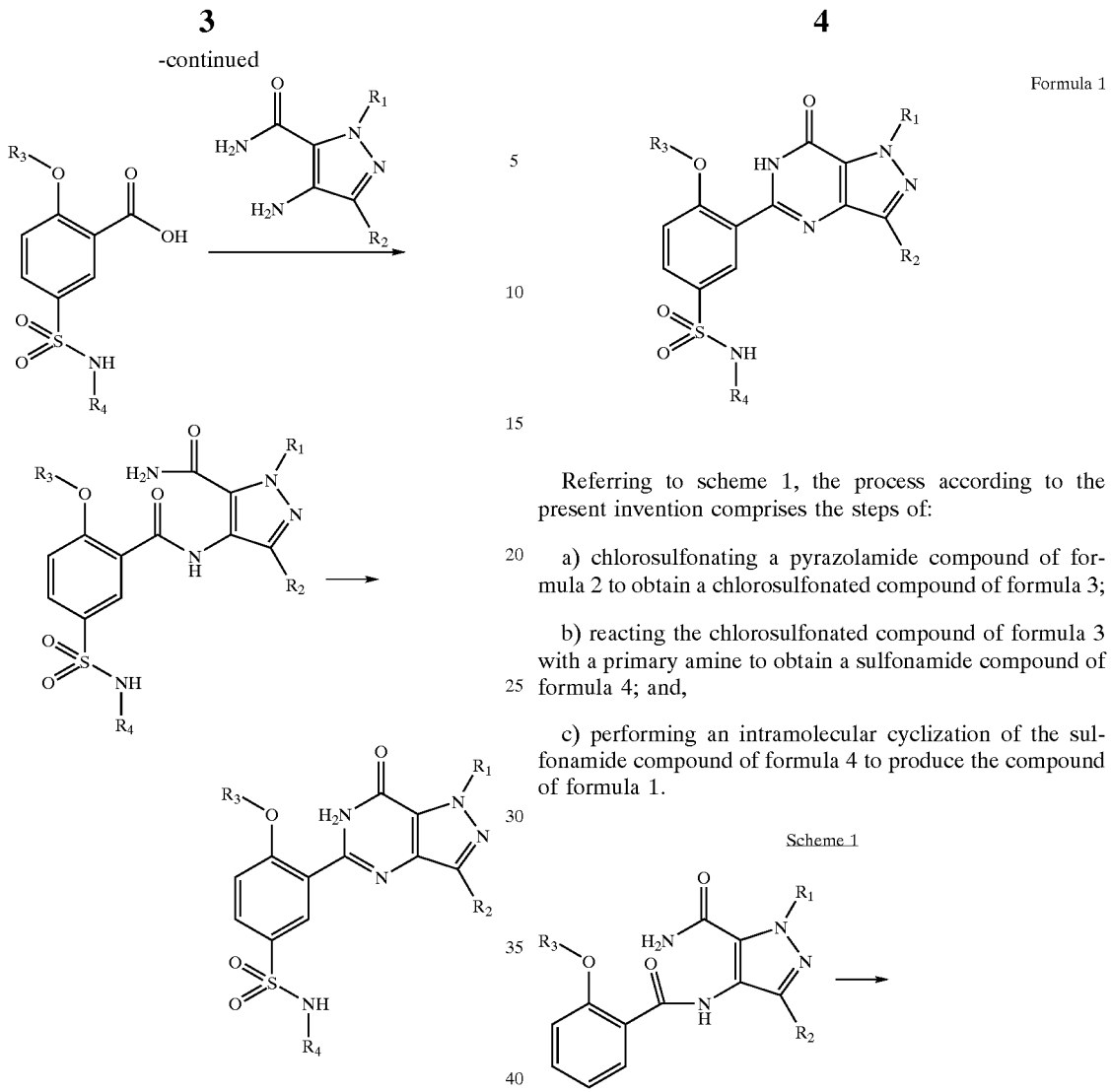

Referring to scheme 1, the process according to the present invention comprises the steps of:

a) chlorosulfonating a pyrazolamide compound of formula 2 to obtain a chlorosulfonated compound of formula 3;

b) reacting the chlorosulfonated compound of formula 3 with a primary amine to obtain a sulfonamide compound of formula 4; and, c) performing an intramolecular cyclization of the sulfonamide compound of formula 4 to produce the compound of formula 1.

However, the said process has several disadvantages. First, the reaction of the sulfonamide-substituted benzoic acid with pyrazolamine in the step b) requires the expensive coupling reagent or activation reagent such as trichloro benzoyl chloride and EEDQ (N-ethoxycarbonyl-2-ethoxy-1,3-dihydroquinoline). Second, the yield of the step a) in which the chlorosulfonated alkoxy bonzoic acid reacts with a primary amine to produce sulfonamide-substituted benzoic acid is somewhat low, and thus, reduces the total yield of the process.

Leading to the present invention, the intensive and thorough research for efficiently preparing the pyrazolopyrimidinone compound useful for the treatment of impotence, carried out by the present inventors aiming to avoid the problems encountered in the prior arts, resulted in the finding that the pyrazolopyrimidinone compound can be prepared under mild condition in high yield, with high purity and in a economic manner by chlorosulfonation, amination with a primary amine and intramolecular cyclization of a pyrazolamide compound obtained by the reaction of alkoxy benzoic acid with pyrazolamine.

Therefore, it is an object of the present invention to provide a process for preparing pyrazolopyrimidinone derivatives of formula 1 and pharmaceutically acceptable salts thereof.

DISCLOSURE OF THE INVENTION

The present invention provides a process for preparing pyrazolopyrimidinone derivatives of formula 1 and pharmaceutically acceptable salts thereof.

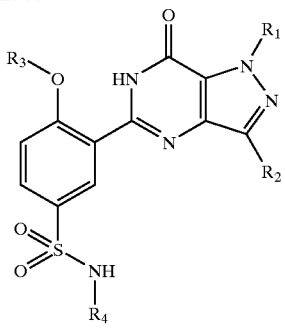

Wherein, $R_1$ represents hydrogen, $C_1$–$C_6$ alkyl, $C_1$–$C_3$ alkyl fluoride or $C_3$–$C_6$ cycloalkyl;

$R_2$ represents hydrogen, substituted or unsubstituted $C_2$–$C_6$ alkyl, $C_1$–$C_3$ alkyl fluoride or $C_3$–$C_6$ cycloalkyl;

$R_3$ represents substituted or unsubstituted $C_1$–$C_6$ alkyl, $C_1$–$C_6$ alkyl fluoride, $C_3$–$C_6$ cycloalkyl, $C_3$–$C_6$ alkenyl or $C_3$–$C_6$ alkynyl; and, $R_4$ represents substituted or unsubstituted $C_1$–$C_{10}$ alkyl, substituted or unsubstituted $C_1$–$C_9$ alkenyl, substituted or unsubstituted $C_3$–$C_6$ cycloalkyl, substituted or unsubstituted benzene, or substituted or unsubstituted heterocycle selected from the group consisting of pyridine, isoxazole, thiazole, pyrimidine, indan, benzthiazole, pyrazole, thiadiazol, oxazole, piperidine, morphorine, imidazole, pyrrolidine, thienyl, triazole, pyrrole and furyl.

As a substituent of $R_2$, $R_3$ and $R_4$, $C_1$–$C_{10}$ alkyl, $C_3$–$C_6$ cycloalkyl, halogen, $C_1$–$C_6$ alkyl fluoride, $C_1$–$C_{10}$ alkyloxy, substituted or unsubstituted bezene, or substituted or unsubstituted heterocycle selected from the group consisting of pyridine, isoxazole, thiazole, pyrimidine, indan, benzthiazole, pyrazole, thiadiazole, oxazole, piperidine, morphorine, imidazole, pyrrolidine, thienyl, triazole, pyrrole, and furyl can be mentioned.

Preferably, $R_1$ represents $C_1$–$C_3$ alkyl; $R_2$ represents substituted or unsubstituted $C_2$–$C_6$ alkyl; $R_3$ represents substituted or unsubstituted $C_2$–$C_6$ alkyl; $R_4$ represents substituted or unsubstituted $C_1$–$C_6$ alkyl, substituted or unsubstituted $C_3$–$C_6$ cycloalkyl, substituted or unsubstituted bezene, substituted or unsubstituted pyridine, or substituted or unsubstituted pyrrole, wherein the substituent of $R_2$, $R_3$ and $R_4$ is halogen, substituted or unsubstituted benzene, substituted or unsubstituted heterocycle selected from the group consisting of pyridine, pyrrolidine, piperidine, pyrrole, and substituted or unsubstituted $C_3$–$C_6$ cycloalkyl.

More preferably, $R_4$ represents substituted $C_1$–$C_6$ alkyl, wherein the substituent is pyrrolidine.

Particularly preferred are as follows:

(1) 5-[2-propoxy-5-(1-methyl-2-pyrrolidinylethyl amidosulfonyl)phenyl]-1-methyl-3-propyl-1,6-dihydro-7H-pyrazolo(4,3-d)pyrimidin-7-one;

(2) 5-[2-propoxy-5-(1-methyl-3-pyrrolidinylmethyl amidosulfonyl)phenyl]-1-methyl-3-propyl-1,6-dihydro-7H-pyrazolo(4,3-d)pyrimidin-7-one; and (3) 5-[2-propoxy-5-(2-pyridylmethyl amidosulfonyl) phenyl]-1-methyl-3-propyl-1,6-dihydro-7H-pyrazolo(4,3-d) pyrimidin-7-one.

Hereinafter, a detailed description will be given of the method of the present invention according to each step.

I. Chlorosulfonation Step (Step a)

4-(2-alkoxy benzamido)-1-alkyl-3-alkyl-5-carbamoyl pyrazole of formula 2 is directly reacted with chlorosulfonic acid or reacted with a mixture of chlorosulfonic acid and suitable amounts of thionyl chloride at an appropriate temperature, 20° C. or lower, to prepare the chlorosulfonated compound of formula 3.

II. Sulfonamidization Step (Step b)

The obtained chlorosulfonated compound is reacted with a primary amine in an appropriate solvent at suitable temperature, to produce the sulfonamide compound of formula 4.

The solvent which can be used in this reaction includes alcohol, dichloromethane and chloroform, but not limited thereto. The skilled in the art would adapt an appropriate solvent in the consideration of the solubility of the starting material, reaction condition, etc.

As a primary amine used, 2-(2-aminoethyl)-1-methylpyrrolidine, 3-aminomethyl-1-methylpyrrolidine or 2-aminomethyl-pyridine can be preferably mentioned. The amount of the primary amine used in this reaction is no less than 2 equivalents based on the chlorosulfonated compound. Alternatively, when acid scavenger such as tertiary amine, which scavenging the acid generated during the reaction, is used, the primary amine can be used in a stoichiometric quantity.

The reaction temperature of this reaction is preferably 20° C. or lower. The sulfonamide compound of formula 4 can be worked up from the reaction mixture and proceeded to the next reaction step c). Or step c) can be performed in situ by just adding a suitable base to the reaction mixture in situ without workup.

III. Intramolecular Cyclization Step (Step c)

Pyrazolopyrimidinone of formula 1 is prepared through intramolecular cyclization of the sulfonamide compound of formula 4. The intramolecular cyclization is carried out in the presence of a suitable base at the appropriate temperature. For example, metal salts of alcohol, metal salts of ammonia, amine, alkali or alkali earth metal hydrides, hydroxides, carbonates, bicarbonates, and bicyclic amidines such as DBU (1,8-diazabicyclo[5.4.0]undec-7-ene) and DBN (1,5-diazabicyclo[4.3.0]non-5-ene) can be mentioned as a suitable base.

The solvent which can be used in the intramolecular cyclization includes alcohol such as methanol, ethanol, isopropanol and t-butanol; ether including tetrahydrofuran, dimethoxyethane and dioxane; aromatic hydrocarbons, such as benzene, toluene, xylene, chloro benzene; acetonitrile, dimethylsulfoxide, dimethylformamide, N-methylpyrrolidin-2-one and pyridine.

The present invention provides the sulfonamide compound of formula 4 from step a) and step b) reaction in good yield and in high purity. And as previously mentioned, the step c) can be performed in situ with the sulfonamide compound of formula 4 produced in the step b) in a one-pot reaction, thereby reducing the overall procedure of the reaction and effectuating the efficient synthesis of pyrazolopyrimidinone compound of formula 1.

In particular, according to the preferred embodiment of the present invention, even though tertiary amine was used as a part of substituent of $R_4$, the yield of the reaction was high.

The present invention also provides a method for preparing pharmaceutically acceptable salts of pyrazolopyrimidinone compound as represented in formula 1, wherein the pharmaceutically acceptable salts of pyrazolopyrimidinone compound can be prepared by adding a pharmaceutically acceptable free acid to the pyrazolopyrimidinone compound of formula 1. Examples of a free acid include inorganic acid, for example, hydrochloric acid, hydrobromic acid, sulfuric acid, phosphoric acid and so on; and organic acids, for example, citric acid, acetic acid, lactic acid, tartaric acid, maleic acid, fumaric acid, gluconic acid, methanesulfonic acid, glycolic acid, succinic acid, p-toluenesulfonic acid, galacturonic acid, embonic acid, glutamic acid, or aspartic acid.

A better understanding of the present invention may be obtained in light of the following examples which are set forth to illustrate, but are not to be construed to limit the present invention.

EXAMPLE

Molecular structures of the present compounds were confirmed by infrared spectrometry, ultraviolet spectrometry, nuclear magnetic resonance spectrometry, mass spectrometry, and elemental analysis of representative compounds by comparing calculated values with observed values.

The pyrazolamide compound of formula 2, which is a starting material of the present invention, can be obtained in high yield by reacting alkoxy benzoic acid with pyrazolamine as illustrated in the scheme 1.

Preparation

Preparation of 4-[2-propoxy benzamido]-1-methyl-3-propyl-5-carbamoyl pyrazole

To a solution of 25 g of 2-propoxy benzoic acid dissolved in dichloromethane, 66 g of thionyl chloride was added and stirred for 3 hours under reflux. After reaction was completed, the solvent and excessive thionyl chloride were distilled off under reduced pressure. To the residue was added 200 ml of dichloromethane (reaction solution 1). In another container, to 24 g of 1-methyl-3-propyl-4-amino-5-carbamoyl pyrazole in dichloromethane was added 13.4 g of triethylamine and 100 mg of dimethylaminopyridine and then cooled to 0° C., to which said reaction solution 1 was slowly added while maintaining the temperature of the solution at 0° C., and then stirred for 1 hour. The reaction mixture was successively washed with water, saturated aqueous sodium bicarbonate solution and brine. The organic layer was dried over anhydrous sodium sulfate and then filtered. The filtrate was concentrated under reduced pressure to obtain a crude product and then triturated with hexane to give 39 g of the title compound.

$^1$H NMR (CDCl$_3$): 0.91 (t, 3H), 1.0.5 (t, 3H), 1.62 (m, 2H), 1.89 (m, 2H), 2.52 (t, 2H), 4.06 (s, 3H), 4.18 (t, 2H), 5.57 (br s, 1H), 7.09 (m, 2H), 7.52 (m, 1H), 7.73 (br s, 1H), 8.26 (dd, 1H), 9.45 (br s, 1H)

Example 1A

Preparation of 5-[2-propoxy-5-(1-methyl-2-pyrolidinylethyl amidosulfonyl)phenyl]-1-methyl-3-propyl-1,6-dihydro-7H-pyrazolo(4,3-d)pyrimidin-7-one (Step a) preparation of 4-[2-propoxy-5-(chlorosulfonyl) benzamido]-1-methyl-3-propyl-5-carbamoyl pyrazole To 23 ml of chlorosulfonic acid cooled to 0° C., 10 g of 4-[2-propoxy benzamido]-1-methyl-3-propyl-5-carbamoyl pyrazole was added and then stirred at room temperature for 2 hours. Reaction mixture was added to ice water of 0° C. and then stirred for 1 hour to obtain white solid, which was filtered and washed with water. The obtained white solid was dissolved in ethyl acetate. The solution was successively washed with water and brine. The organic layer was dried over anhydrous magnesium sulfate and filtered. The filtrate was concentrated under reduced pressure to obtain a crude product and triturated with hexane to give 9.14 g of the title compound.

$^1$H NMR (CDCl$_3$): 0.92 (t, 3H), 1.08 (t, 3H), 1.62 (m, 2H), 1.97 (m, 2H), 2.50 (t, 2H), 4.04 (s, 3H), 4.32 (t, 2H), 5.63 (br s, 1H), 7.24 (d, 1H), 7.54 (br s, 1H), 8.15 (dd, 1H), 8.93 (d, 1H), 9.17 (br s, 1H)

(Step 2) preparation of 4-[2-propoxy-5-(1-methyl-2-pyrolidinylethyl amidosulfonyl)benzamido]-1-methyl-3-propyl-5-carbamoyl pyrazole To 9.14 g of 4-[2-propoxy-5-(chlorosulfonyl) benzamido]-1-methyl-3-propyl-5-carbamoyl pyrazole in dichloromethane, 5 ml of 2-(2-aminoethyl)-1-methyl pyrrolidine was added at 0° C. and stirred for 1 hour at room temperature. After completion of reaction, the reaction solution was diluted with dichloromethane. The solution was successively washed with saturated sodium bicarbonate solution, water and brine. The organic layer was dried over anhydrous sodium sulfate and filtered. The filtrate was concentrated under reduced pressure to produce a crude product and triturated with a mixture of hexane:ethyl acetate (10:1) to give 9.69 g of the pure title compound.

$^1$H NMR (CDCl$_3$): 0.90 (t, 3H), 1.06 (t, 3H), 1.59 (m, 2H), 1.70 (m, 6H), 1.93 (m, 2H), 2.15 (m, 1H), 2.29 (s, 3H), 2.39 (m. 1H), 2.49 (t, 2H), 3.04 (m, 3H), 4.02 (s, 3H), 4.24 (t, 2H), 5.82 (br s, 1H), 7.13 (d, 1H). 7.58 (br s, 1H), 7.96 (dd, 1H), 8.67 (d, 1H), 9.26 (br s, 1H)

(Step 3) preparation of 5-[2-propoxy-5-(1-methyl-2-pyrolidinylethyl amidosulfonyl)phenyl]-1-methyl-3-propyl-1,6-dihydro-7H-pyrazolo(4,3-d)pyrimidin-7-one To a solution of 9.59 of 4-[2-propoxy-5-(1-methyl-2-pyrolidinylethyl amidosulfonyl)benzamido]-1-methyl-3-propyl-5-carbamoyl pyrazole dissolved in 192 ml of t-butanol, 4.02 g of potassium t-butoxide was added and then stirred for 8 hours under reflux. After completion of reaction, the reaction solution was cooled to room temperature and diluted with ethyl acetate. The solution was successively washed with water and brine. The organic layer was dried over anhydrous magnesium sulfate and filtered. The filtrate was vacuum-distilled to remove the solvent. Column chromatography of the residue on silica gel gave 7 g of the pure title compound.

$^1$H NMR (CDCl$_3$): 0.99 (t, 3H), 1.15 (t, 3H), 1.56 (m, 4H), 1.79 (m, 4H), 2.02 (m, 3H), 2.28 (s, 3H), 2.36 (m, 1H), 2.89 (t, 2H), 3.07 (m, 3H), 4.23 (t, 2H), 4.24 (s, 3H), 7.11 (d, 1H), 7.92 (dd, 1H), 8.88 (d, 1H)

Example 1B

Preparation of 5-[2-propoxy-5-(1-methyl-2-pyrolidinylethyl amidosulfonyl)phenyl]-1-methyl-3-propyl-1,6-dihydro-7H-pyrazolo(4,3-d)pyrimidin-7-one (Step 1) preparation of 4-[2-propoxy-5-(chlorosulfonyl) benzamido]-1-methyl-3-propyl-5-carbamoyl pyrazole To 32.8 ml of chlorosulfonic acid cooled to 0° C., 8.48 ml of thionyl chloride and 20 g of 4-[2-propoxy benzamido]-1-methyl-3-propyl-5-carbamoyl pyrazole were successively added dropwise and portionwise, and then stirred for 2 hours at room temperature. Reaction mixture was added to ice water of 0° C. After 1 hour, the reaction mixture was extracted with ethyl acetate. The organic solution was successively washed with water and brine. The organic layer was dried over anhydrous magnesium sulfate and filtered. The filtrate was concentrated under reduced pressure to obtain a crude product and triturated with a mixture of hexane:ethyl acetate (10:1) to give 23 g of the title compound.

$^1$H NMR(CDCl$_3$): 0.92 (t, 3H), 1.08 (t, 3H), 1.62 (m, 2H), 1.97 (m, 2H), 2.50 (t, 2H), 4.04 (s, 3H), 4.32 (t, 2H), 5.63 (br s, 1H), 7.24 (d, 1H), 7.54 (br s, 1H), 8.15 (dd, 1H), 8.93 (d, 1H), 9.17 (br s, 1H).

(Steps 2 and 3) preparation of 5-[2-propoxy-5-(1-methyl-2-pyrolidinylethyl amidosulfonyl)phenyl]-1-methyl-3-propyl-1,6-dihydro-7H-pyrazolo(4,3-d)pyrimidin-7-one To 20.8 g of 4-[2-propoxy-5-(chlorosulfonyl) benzamido]-1-methyl-3-propyl-5-carbamoyl pyrazole in ethanol, 11.3 ml of 2-(2-aminoethyl)-1-methyl pyrrolidine was added at 0° C. and stirred for 1 hour at room temperature. To this solution, 12 g of sodium ethoxide was added and stirred for 5 hours under reflux. After completion of reaction, the reaction solution was cooled to room temperature and adjusted to pH 9 by concentrated hydrochloric acid. The reaction solution was diluted with dichloromethane. The solution was successively washed with water and brine. The organic layer was dried over anhydrous sodium sulfate and filtered. The filtrate was concentrated under reduced pressure to remove the solvent, which was then recrystallized with ethanol to give 18.4 g of the pure title compound.

$^1$H NMR(CDCl$_3$): 0.99 (t, 3H), 1.15 (t, 3H), 1.56 (m, 4H), 1.79 (m, 4H), 2.02 (m, 3H), 2.28 (s, 3H), 2.36 (m, 1H), 2.89 (t, 2H), 3.07 (m, 3H), 4.23 (t, 2H), 4.24 (s, 3H), 7.11 (d, 1H), 7.92 (dd, 1H), 8.88 (d, 1H).

Example 2

Preparation of 5-[2-propoxy-5-(1-methyl-3-pyrolidinylmethyl amidosulfonyl)phenyl]-1-methyl-3-propyl-1,6-dihydro-7H-pyrazolo(4,3-d)pyrimidin-7-one (Step 1) preparation of 4-[2-propoxy-5-(chlorosulfonyl) benzamido]-1-methyl-3-propyl-5-carbamoyl pyrazole The title compound was produced in the same manner as in the step 1 of the above example 1B.

(Step 2) preparation of 4-[2-propoxy-5-(1-methyl-3-pyrrolidinylmethyl amidosulfonyl)benzamido]-1-methyl-3-propyl-5-carbamoyl pyrazole To 1.0 g of 4-[2-propoxy-5-(chlorosulfonyl) benzamido]-1-methyl-3-propyl-5-carbamoyl pyrazole in dichloromethane, 516 mg of 3-aminomethyl-1-methyl pyrrolidine was added at 0° C. and stirred for 1 hour at room temperature. After completion of reaction, the reaction solution was diluted with dichloromethane. The solution was successively washed with saturated sodium bicarbonate solution, water and brine. The organic layer was dried over anhydrous sodium sulfate and filtered. The filtrate was concentrated under reduced pressure to give a crude product and triturated with hexane to give 825 mg of the pure title compound.

$^1$H NMR(CDCl$_3$): 0.91 (t, 3H), 1.06 (t, 3H), 1.60 (m, 3H), 1.99 (m, 3H), 2.34 (s, 3H), 2.40 (m, 6H), 2.85 (m, 1H), 2.94 (d .2H), 4.03 (s, 3H), 4.24 (t, 2H), 5.82 (br s, 1H), 7.13 (d, 1H). 7.58 (br s, 1H), 7.99 (dd, 1H), 8.88 (d, 1H), 9.29 (br s, 1H).

(Step 3) preparation of 5-[2-propoxy-5-(1-methyl-3-pyrrolidinylmethyl amidosulfonyl)phenyl]-1-methyl-3-propyl-1,6-dihydro-7H-pyrazolo(4,3-d)pyrimidin-7-one To a solution of 825 mg of 4-[2-propoxy-5-(1-methyl-3-pyrrolidinylmethyl amidosulfonyl) benzamido]-1-methyl-3-propyl-5-carbamoyl pyrazole dissolved in 10 ml of t-butanol, 213 mg of potassium t-butoxide was added and then stirred for 8 hours under reflux. After completion of reaction, the reaction solution was cooled to room temperature and diluted with dichloromethane. The solution was successively washed with water and brine. The organic layer was dried over anhydrous sodium sulfate and filtered. The filtrate was concentrated under reduced pressure to remove the solvent. Column chromatography of the crude product on silica gel gave 719 mg of the pure title compound.

$^1$H NMR(CDCl$_3$): 1.00 (t, 3H), 1.16 (t, 3H), 1.60 (m, 1H), 1.82 (m, 2H), 2.02 (m, 3H), 2.38 (s, 3H), 2.50 (m, 4H), 2.90 (t, 2H), 3.01 (d, 2H), 4.23 (t, 2H), 4.25 (s, 3H), 7.12 (d, 1H), 7.94 (dd, 1H), 8.88 (d, 1H).

Example 3

Preparation of 5-[2-propoxy-5-(2-pyridylmethyl amidosulfonyl)phenyl]-1-methyl-3-propyl-1,6-dihydro-7H-pyrazolo(4,3-d)pyrimidin-7-one (Step 1) preparation of 4-[2-propoxy-5-(chlorosulfonyl) benzamido]-1-methyl-3-propyl-5-carbamoyl pyrazole The title compound was prepared in the same manner as in the step 1 of the above example 1B.

(Step 2) preparation of 4-[2-propoxy-5-(2-pyridylmethyl amidosulfonyl)benzamido]-1-methyl-3-propyl-5-carbamoyl pyrazole To 1.0 g of 4-[2-propoxy-5-(chlorosulfonyl) benzamido]-1-methyl-3-propyl-5-carbamoyl pyrazole in dichloromethane, 0.47 ml of 2-aminomethyl-pyridine was added at 0° C. and stirred for 1 hour at room temperature. After completion of reaction, the reaction solution was diluted with dichloromethane. The solution was successively washed with saturated sodium bicarbonate solution, water and brine. The organic layer was dried over anhydrous sodium sulfate and filtered. The filtrate was concentrated under reduced pressure to furnish a crude product and triturated with hexane to give 955 mg of the pure title compound.

$^1$H NMR(CDCl$_3$): 0.90 (t, 3H), 1.05 (t, 3H), 1.59 (m, 2H), 1.90 (m, 2H), 2.49 (t, 2H), 2.65 (br s, 1H), 4.02 (s, 3H), 4.25 (t, 2H), 4.28 (d, 2H), 5.79 (br s, 1H), 6.28 (t, 1H), 7.09 (d, 1H). 7.26 (d, 1H), 7.16 (m, 1H), 7.61 (m, 1H), 7.99 (dd, 1H), 8.42 (d, 1H), 8.69 (d, 1H), 9.22 (br s, 1H).

(Step 3) preparation of 5-[2-propoxy-5-(2-pyridylmethyl amidosulfonyl)phenyl]-1-methyl-3-propyl-1,6-dihydro-7H-pyrazolo(4,3-d)pyrimidin-7-one To a solution of 955 mg of 4-[2-propoxy-5-(2-pyridylmethyl amidosulfonyl)benzamido]-1-methyl-3-propyl-5-carbamoyl pyrazole dissolved in 12 ml of t-butanol, 244 mg of potassium t-butoxide was added and then stirred for 8 hours under reflux. After completion of reaction, the reaction solution was cooled to room temperature and diluted with ethyl acetate. The solution was successively washed with water and brine. The organic layer was dried over anhydrous sodium sulfate and filtered. The filtrate was concentrated under reduced pressure to remove the solvent. The reidue was column chromatographed on silica gel to give 821 mg of the pure title compound.

$^1$H NMR(CDCl$_3$): 1.02 (t, 3H), 1.15 (t, 3H), 1.85 (m, 2H), 2.04 (m, 2H), 2.93 (t, 2H), 4.21 (t, 2H), 4.26 (s, 3H), 4.41 (d, 2H), 6.30 (t, 1H), 7.09 (d, 1H), 7.30 (m, 1H), 7.39 (d, 1H), 7.77 (m, 1H), 7.96 (dd, 1H), 8.45 (d, 1H), 8.86 (d, 1H), 10.82 (br s, 1H).

According to the present invention, pyrazolopyrimidinone derivatives of formula 1 can be prepared in high yield with high purity. In addition, the inexpensive reagents can be used such that they can be prepared in an economic manner.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing pyrazolopyrimidinone derivatives of formula 1, as represented in the following scheme 1, comprising the following steps of:

a) chlorosulfonating a pyrazolamide compound of formula 2 to obtain a chlorosulfonated compound of formula 3;

b) reacting the chlorosulfonated compound of formula 3 with a primary amine to obtain a sulfonamide compound of formula 4; and, c) performing an intramolecular cyclization of the sulfonamide compound of formula 4 to produce the compound of formula 1, wherein the step b) and c) are performed in situ in alcohol by adding a base to the reaction mixture without workup after the step b) is completed:

Scheme 1

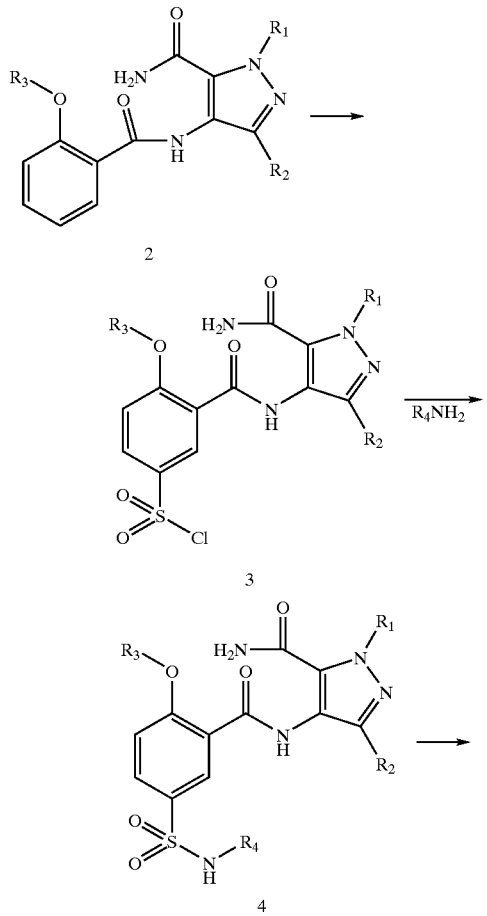

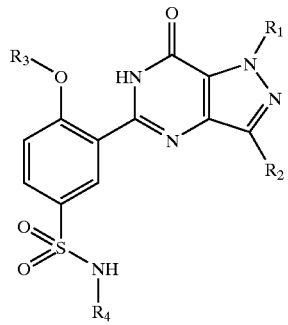

wherein $R_1$ represents hydrogen; $C_1$–$C_6$ alkyl; $C_1$–$C_3$ alkyl fluoride; or $C_3$–$C_6$ cycloalkyl, $R_2$ represents hydrogen; substituted or unsubstituted $C_2$–$C_6$ alkyl; $C_1$–$C_3$ alkyl fluoride; or $C_3$–$C_6$ cycloalkyl, $R_3$ represents substituted or unsubstituted $C_1$–$C_6$ alkyl; $C_1$–$C_6$ alkyl fluoride; $C_3$–$C_6$ cycloalkyl; $C_3$–$C_6$ alkenyl; or $C_3$–$C_6$ alkynyl, and $R_4$ represents substituted or unsubstituted $C_1$–$C_{10}$ alkyl; substituted or unsubstituted $C_1$–$C_9$ alkenyl; substituted or unsubstituted $C_3$–$C_6$ cycloalkyl; substituted or unsubstituted bezene; or substituted or unsubstituted heterocycle selected from the group consisting of pyridine, isoxazole, thiazole, pyrimidine, indan, benzthiazole, pyrazole, thiadiazol, oxazole, piperidine, morphorine, imidazole, pyrrolidine, thienyl, triazole, pyrrole and furyl, in which, substituents usable for $R_2$, $R_3$ and $R_4$ comprises $C_1$–$C_{10}$ alkyl; $C_3$–$C_6$ cycloalkyl; halogen; $C_1$–$C_6$ alkyl fluoride; $C_1$–$C_{10}$ alkyloxy; substituted or unsubstituted bezene; or substituted or unsubstituted heterocycle selected from the group consisting of pyridine, isoxazole, thiazole, pyrimidine, indan, benzthiazole, pyrazole, thiadiazole, oxazole, piperidine, morphorine, imidazole, pyrrolidine, thienyl, triazole, pyrrole, and furyl.

2. The method according to claim 1, wherein $R_1$ represents $C_1$–$C_3$ alkyl, $R_2$ represents substituted or unsubstituted $C_2$–$C_6$ alkyl, $R_3$ represents substituted or unsubstituted $C_2$–$C_6$ alkyl, and $R_4$ represents substituted or unsubstituted $C_1$–$C_6$ alkyl, substituted or unsubstituted $C_3$–$C_6$ cycloalkyl, substituted or unsubstituted bezene, substituted or unsubstituted pyridine, or substituted or unsubstituted pyrrole, in which, substituents usable for $R_2$, $R_3$ and $R_4$ comprises halogen, substituted or unsubstituted benzene, substituted or unsubstituted heterocycle selected from the group consisting of pyridine, pyrrolidine, piperidine, pyrrole, and substituted or unsubstituted $C_3$–$C_6$ cycloalkyl.

3. The method according to claim 1, wherein said derivative of formula 1 is selected from the group consisting of 5-[2-propoxy-5-(1-methyl-2-pyrrolidinylethyl amidosulfonyl)phenyl]-1-methyl-3-propyl-1,6-dihydro-7H-pyrazolo(4,3-d)pyrimidin-7-one, 5-[2-propoxy-5-(1-methyl-3-pyrrolidinylmethyl amidosulfonyl) phenyl]-1-methyl-3-propyl-1,6-dihydro-7H-pyrazolo(4,3-d)pyrimidin-7-one, and 5-[2-propoxy-5-(2-pyridylmethyl amidosulfonyl)phenyl]-1-methyl-3-propyl-1,6-dihydro-7H-pyrazolo(4,3-d)pyrimidin-7-one.

4. The method according to claim 1, wherein said step a) is carried out at about 20° C. or lower.

5. The method according to claim 1, wherein said step b) is carried out at about 20° C. or lower.

6. The method according to claim 1, wherein said alcohol is ethanol.

7. The method according to claim 1, wherein the said c) is performed in the presence of a base selected from the group consisting of metal salts of alcohols, metal salts of ammonia, amines, alkali or alkali earth metal hydrides, hydroxides, carbonates, bicarbonates, an bicyclic amidines such as DBU (1,8-diazabicyclo[5.4.0]undec-7-ene) and DBN (1,5-diazabicyclo[4.3.0.]non-5-ene).

8. A method for preparing salts of pyrazolopyrimidinone derivatives of formula 1 by reacting pyrazolopyrimidinone compounds obtained by the method of claim 1 with a free acid.

9. The method according to claim 8, wherein said free acid is selected from the group consisting of hydrochloric acid, hydrobromic acid, sulfuric acid, posphoric acid, citric acid, acetic acid, lactic acid, tartaric acid, maleic acid, fumaric acid, gluconic acid, methanesulfonic acid, glycolic acid, succinic acid, p-toluenesulfonic acid, galacturonic acid, embonic acid, glutamic acid and aspartic acid.

* * * * *

UNITED STATES PATENT AND TRADEMARK OFFICE
CERTIFICATE OF CORRECTION

PATENT NO. : 6,844,436 B2
DATED : January 18, 2005
INVENTOR(S) : Moo-Hi Yoo et al.

It is certified that error appears in the above-identified patent and that said Letters Patent is hereby corrected as shown below:

Column 13,
Line 11, the word "an" should be corrected to -- and --.

Column 14,
Line 7, the word "posphoric" should be corrected to -- phosphoric --.

Signed and Sealed this

Nineteenth Day of July, 2005

JON W. DUDAS
*Director of the United States Patent and Trademark Office*